United States Patent
Kusch et al.

(10) Patent No.: US 7,200,202 B2
(45) Date of Patent: Apr. 3, 2007

(54) LINEAR ACCELERATOR WITH X-RAY IMAGING ELEMENTS MOUNTED ON ROTATING SUPPORT

(75) Inventors: Jochen Klaus Kusch, Concord, CA (US); David Brown, Tracy, CA (US); Michelle Marie Svatos, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/861,717

(22) Filed: Jun. 3, 2004

(65) Prior Publication Data

US 2005/0281387 A1    Dec. 22, 2005

(51) Int. Cl.
*A61N 5/10*   (2006.01)
*A61B 6/00*   (2006.01)

(52) U.S. Cl. .............................. 378/65; 378/9; 378/19; 378/197; 600/436

(58) Field of Classification Search .................. 378/4, 378/9, 15, 20, 21, 22, 27, 39, 41, 62, 65, 378/91, 95, 98, 98.12, 145, 189, 193, 195, 378/196, 197, 198, 204, 205, 901, 98.9, 19; 250/354.1, 370.08, 370.09, 370.1; 600/407, 600/436
See application file for complete search history.

(56) References Cited

U.S. PATENT DOCUMENTS

| 6,842,502 | B2 * | 1/2005 | Jaffray et al. | 378/65 |
| 6,865,254 | B2 * | 3/2005 | Nafstadius | 378/65 |
| 6,888,919 | B2 * | 5/2005 | Graf | 378/65 |
| 6,914,959 | B2 * | 7/2005 | Bailey et al. | 378/65 |

\* cited by examiner

*Primary Examiner*—Edward J. Glick
*Assistant Examiner*—Anastasia S. Midkiff

(57) ABSTRACT

A system according to some embodiments may include a treatment head to emit treatment radiation, a gantry coupled to the treatment head, an x-ray tube to emit imaging radiation, an imaging device to acquire an image based on the imaging radiation, and a support. The support may be coupled to the x-ray tube and to the imaging device, and movably coupled to the gantry for movement independent of gantry.

13 Claims, 5 Drawing Sheets

LINEAR ACCELERATOR WITH X-RAY IMAGING ELEMENTS MOUNTED ON ROTATING SUPPORT

BACKGROUND

1. Field

The embodiments described below relate generally to radiation treatment, and more particularly to imaging systems used in conjunction with such treatment.

2. Description

According to conventional radiation treatment, a beam of treatment radiation is directed toward a tumor located within a patient. The radiation beam delivers a predetermined dose of therapeutic radiation to the tumor according to an established treatment plan. The delivered radiation kills cells of the tumor by causing ionizations within the cells.

Treatment plans are therefore designed to maximize radiation delivered to a target while minimizing radiation delivered to healthy tissue. However, a treatment plan is designed assuming that relevant portions of a patient will be in a particular position relative to a treatment device during treatment. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

Due to the foregoing, treatment plans are designed under the assumption that positioning errors may occur that may result in misdelivery of radiation. Treatment plans compensate for this potential misdelivery by specifying lower doses or smaller beam shapes (e.g., beams that do not radiate edges of a tumor) than would be specified if misdelivery was not expected. Such compensation may decrease as margins of error in patient positioning decrease.

It would therefore be beneficial to provide a system and method that may increase the accuracy of patient positioning during radiation treatment. When used in conjunction with conventionally-designed treatments, more accurate positioning may reduce chances of harming healthy tissue. More accurate patient positioning may also allow the use of more aggressive treatments. Specifically, if a margin of error in patient positioning is known to be small, treatment may be designed to safely radiate a greater portion of a tumor with higher doses than in scenarios where the margin of error is larger.

Recent systems attempt to improve the accuracy of patient positioning by combining a device for emitting treatment radiation with a device for emitting radiation that is more suitable for creating images. In one example, a fixed device is provided to deliver imaging radiation perpendicularly to the direction of treatment radiation and toward a fixed imaging device. The perspective provided by a resulting image is not particularly useful in determining whether a tumor or body of interest is properly positioned with respect to the treatment head.

SUMMARY

To address at least the above problems, some embodiments provide a system, method, medium, apparatus, and means to emit imaging radiation towards a patient disposed in a first position using an x-ray tube, acquire an image based on the imaging radiation using an imaging device, emit treatment radiation towards the patient disposed in the first position using a treatment head, and move the x-ray tube and the imaging device independently of the treatment head. Some embodiments further provide rotation of the x-ray tube and the imaging device about an axis by rotation of a support coupled to the x-ray tube and to the imaging device.

According to some embodiments, provided are a treatment head to emit treatment radiation towards a patient disposed in a first position, an x-ray tube to emit imaging radiation towards the patient disposed in the first position, and an imaging device to acquire an image based on the imaging radiation, wherein the x-ray tube and the imaging device are moveable independently of the treatment head. Embodiments may further include a gantry coupled to the treatment head, the gantry rotatable to rotate the treatment head about a first axis. In an even further aspect, a support may be coupled to the x-ray tube and to the imaging device, the support being rotatable to rotate the x-ray tube and the imaging device about a second axis.

Some embodiments provide a treatment head to emit treatment radiation, a gantry coupled to the treatment head, an x-ray tube to emit imaging radiation, an imaging device to acquire an image based on the imaging radiation, and a support coupled to the x-ray tube and to the imaging device, and movably coupled to the gantry for movement independently of the gantry. The gantry may be rotatable to rotate the treatment head about a first axis. Also, the support may be rotatably coupled to the gantry to rotate the x-ray tube and the imaging device about a second axis.

Embodiments may also include emission of imaging radiation using an x-ray tube, acquisition of an image based on the imaging radiation using an imaging device, emission of treatment radiation using a treatment head coupled to a gantry, and movement of a support independently of the gantry, wherein the support is coupled to the x-ray tube, to the imaging device, and to the gantry. According to some embodiments movement of the support includes rotation of the support to rotate the x-ray tube and the imaging device about a second axis.

In some embodiments, provided are acquisition of a three-dimensional image of a patient in a first position to receive treatment radiation, and determination of whether the first position complies with a treatment plan based on the three-dimensional image. Further, embodiments may provide delivery of the treatment radiation to the patient if it is determined that the first position complies with the treatment plan. Embodiments may also or alternatively provide acquisition of a plurality of projection images of the patient in the first position, and creation of the three-dimensional image based on the plurality of projection images.

According to some embodiments, included are an imaging system to acquire a three-dimensional image of a patient in a first position to receive treatment radiation, and a processor to determine whether the first position complies with a treatment plan based on the three-dimensional image. Also included are a treatment head to deliver the treatment radiation to the patient if it is determined that the first position complies with the treatment plan. The imaging system may include an x-ray tube to emit imaging radiation, an imaging device to acquire a projection image based on the imaging radiation, and a support coupled to the x-ray tube and to the imaging device, and movable to rotate the x-ray tube and the imaging device around the patient.

The claims are not limited to the disclosed embodiments, however, as those skilled in the art can readily adapt the teachings herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the claimed invention and sets forth the best mode contemplated by the inventors for carrying out the claimed invention. Various modifications, however, will remain readily apparent to those in the art.

Figure 1:
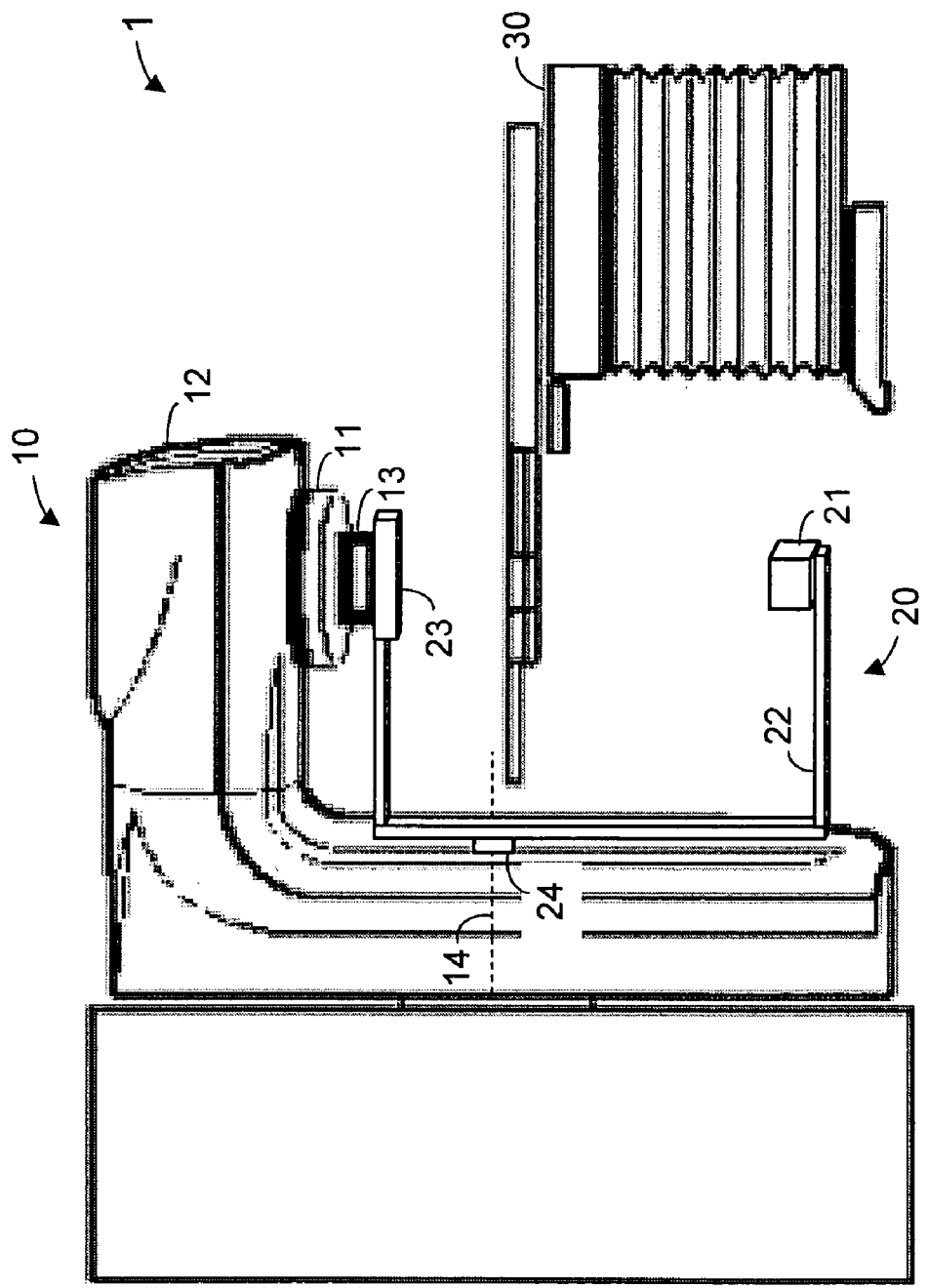
FIG. 1 is a view of a radiation treatment system according to some embodiments.

FIG. 1 illustrates radiation treatment room 1 pursuant to some embodiments. Radiation treatment room 1 includes linear accelerator (linac) 10, imaging system 20, and table 30. The elements of radiation treatment room 1 may be used to deliver treatment radiation to a patient according to a radiation treatment plan.

Linac 10 generates and emits the treatment radiation, and is primarily composed of treatment head 11 and gantry 12. Treatment head 11 includes a beam-emitting device (not shown) for emitting a radiation beam used during calibration, verification, and/or treatment. The radiation beam may comprise electron, photon or any other type of radiation. According to some embodiments, the treatment radiation comprises megavoltage radiation. Also included within treatment head 11 is a beam-shielding device, or collimator (not shown) for shaping the beam and for shielding sensitive surfaces from the beam.

Accessory tray 13 is mounted on treatment head 11 and may be configured to receive and securely hold attachments used during the course of treatment planning and treatment. These attachments may include reticles, wedges, or the like for further defining field sizes and intensities.

Treatment head 11 is fastened to a projection of gantry 12. Gantry 12 is rotatable around gantry axis 14 before, during and after radiation treatment. In some embodiments, gantry 12 may rotate clockwise and counter-clockwise around axis 14. Rotation of gantry 12 serves to rotate treatment head 11 around axis 14.

During radiation treatment, treatment radiation is delivered from linac 10 to the beam-emitting device of treatment head 11 and is emitted therefrom as a divergent beam. The beam is emitted towards a point, known as the isocenter, which may be located at the intersection of an axis of the beam and gantry axis 14. Due to divergence of the radiation beam and the shaping of the beam by the aforementioned beam-shaping devices, the beam may deliver radiation to a multi-dimensional radiation field rather than only to the isocenter.

Imaging system 20 may be used to acquire images that may be used before, during and/or after radiation treatment. For example, imaging system 20 may be used to acquire images for verification and recordation of a patient position and of an internal patient portal to which radiation is delivered. Images acquired by imaging device 20 may also be used according to some embodiments of the invention to provide four-dimensional fluoroscopy of radiation treatment.

Imaging system 20 comprises x-ray tube 21, support 22, imaging device 23, and coupling 24. X-ray tube 21 and imaging device 23 may be moveable independently of treatment head 11. According to one specific example of the foregoing, support 22 is rotatable to rotate x-ray tube 21 and imaging device 23 around axis 14 independent from any rotation of gantry 12. In some embodiments, support 22 is rotatable to rotate x-ray tube 21 and imaging device 23 around an axis different from axis 14.

According to some embodiments, x-ray tube 21 may emit imaging radiation and imaging device 23 may acquire an image based on the imaging radiation at any point during their rotation around axis 14. Imaging device 23 may therefore acquire a plurality of projection images of a body disposed between x-ray tube 21 and imaging device 23, with some of the images having different perspectives. These images may be used to create a three-dimensional cone beam reconstruction image according to currently- or hereafter-known techniques.

X-ray tube 21 may comprise any suitable device to emit imaging radiation, including but not limited to a Diabolo™ x-ray tube. In some embodiments, x-ray tube 21 emits kilovoltage radiation having energies ranging from 50 to 150 keV. Kilovoltage radiation may produce clearer images than megavoltage radiation when used in conjunction with certain imaging devices. Imaging device 23 may comprise a flat-panel imaging device using a scintillator layer and solid-state amorphous silicon photodiodes deployed in a two-dimensional array. The RID1640, offered by Perkin-Elmer®, Inc. of Fremont, Calif., is one suitable device. X-ray tube 21 and imaging device 23 may be coupled to support 22 in any suitable manner.

In operation, the scintillator layer receives x-rays and generates light in proportion to the intensity of the received x-rays. The array of photodiodes receives the light and records the intensity of received light as stored electrical charge. The stored charge therefore comprises an acquired image that represents intensities at each location of a radiation field produced by a radiation beam. The bounds of the radiation field are determined by the physical intersection of the radiation beam with the surface of the scintillator layer.

Imaging device 23 may comprise other types of imaging devices. For example, X-ray radiation may also be converted to and stored as electrical charge without use of a scintillator layer. In such imaging devices, x-rays are absorbed directly by an array of amorphous selenium photoconductors. The photoconductors convert the x-rays directly to stored electrical charge that comprises an acquired image of a radiation field. Imaging device 23 may also comprise a CCD or tube-based camera. Such an imaging device may include a light-proof housing within which are disposed a scintillator, a mirror, and a camera.

Support 22 may comprise any suitable structure. Support 22 may comprise a single integral element or several elements. Support 22 may include various elements for coupling to x-ray tube 21 and/or to imaging device 23. According to some embodiments, support 22 comprises a currently- or hereafter-known "U-arm" for supporting and x-ray tube and an imaging device.

Coupling 24 couples support 22 to gantry 12. Coupling 24 may comprise a rotating coupling such as, but not limited to, a rotational bearing to facilitate the rotation of support 22 independently of any rotation of gantry 12.

Table 30 supports a patient during radiation treatment. Table 30 may be adjustable to assist in positioning a treatment area of the patient at the isocenter of linac 10. Table 30 may also be used to support devices used for calibration and/or verification.

Each of the devices shown in FIG. 1 may include less or more elements than those shown. In addition, embodiments are not limited to the devices shown in FIG. 1.

Figure 2A:
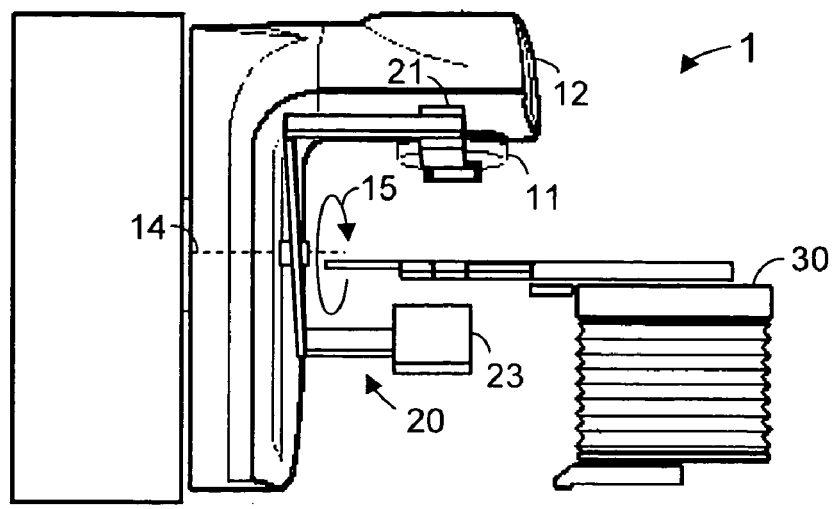
FIGS. 2A and 2B are views of a radiation treatment system in different configurations according to some embodiments.
Figure 2B:
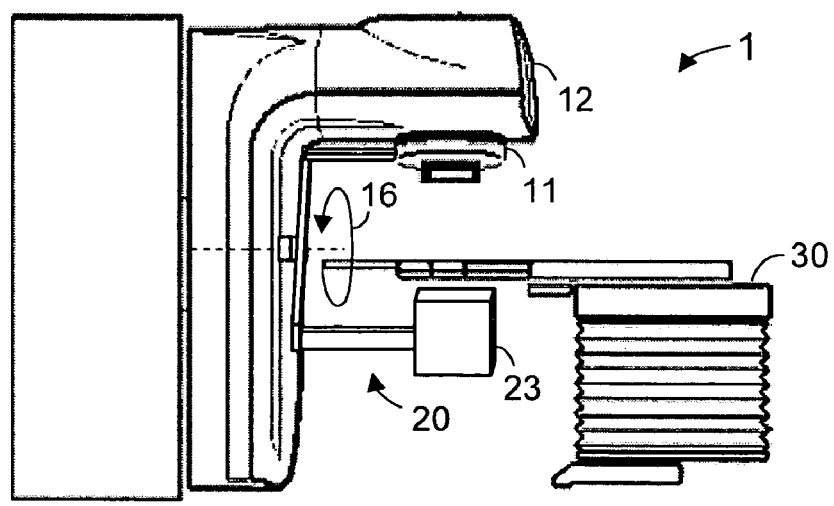

FIGS. 2A and 2B are views of system 1 in various configurations that are different from the configuration shown in FIG. 1. For example, FIG. 2A shows imaging system 20 rotated from the position shown in FIG. 1 in the direction indicated by arrow 15. The rotation has caused x-ray tube 21 to approach treatment head 11, and imaging device 23 to move below and to the side of table 30. Imaging system 20 may be prevented from rotating further in the direction of arrow 15 to avoid a collision between x-ray tube 21 and gantry 12. In some embodiments, a distance between axis 14 and x-ray tube 21 allows x-ray tube 21 to pass under treatment head 11 during the rotation of imaging system 20.

FIG. 2B illustrates imaging system 20 rotated from the position shown in FIG. 1 in the direction indicated by arrow 16. X-ray tube 21 has approached treatment head 11, but is obscured by gantry 12. Accordingly, further rotation of imaging system 20 in the direction of arrow 16 may cause a collision between x-ray tube 21 and gantry 12 in the illustrated embodiment.

As mentioned above, x-ray tube 21 may emit imaging radiation and imaging device 23 may acquire, based on the imaging radiation, an image of an intervening body such as a patient on table 30 at any position of rotation in the direction of arrows 15 and 16 according to some embodiments. A larger distance between x-ray tube 21 and imaging device 23 may provide more efficient acquisition of images than a shorter distance. Several of the images may comprise projection images that may be used to acquire a three-dimensional image. The three-dimensional image may be generated using currently- or hereafter-known cone beam reconstruction techniques or any other suitable technique.

In some embodiments, gantry 12 may move independently of imaging system 20. Gantry 12 may therefore be positioned at any point of rotation around axis 14 in FIGS. 2A and 2B according to some embodiments.

Figure 3:
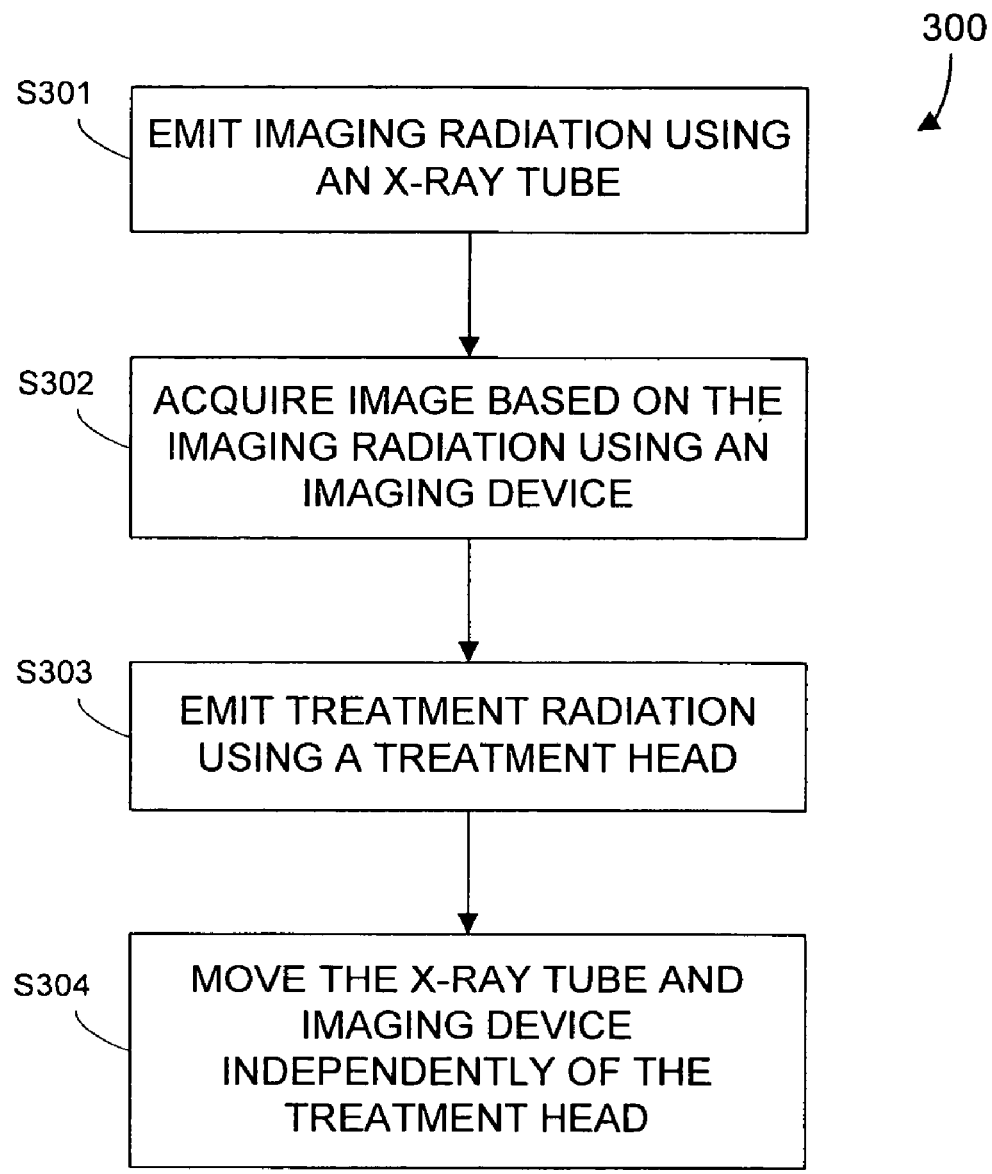
FIG. 3 is a flow diagram of process steps according to some embodiments.

FIG. 3 is a flow diagram of process steps 300 according to some embodiments. Process steps 300 may be embodied, in whole or in part, by hardware of and/or software executed by devices including but not limited to those of linac 10 and imaging system 20.

Process steps 300 may be stored by any medium, including a fixed disk, a floppy disk, a CD-ROM, a DVD-ROM, a Zip™ disk, a magnetic tape, or a signal. Some or all of process steps 300 may also be stored in one or more devices. Moreover, some or all of the process steps 300 may be implemented in hardware, such as a hardware card installed in and/or discrete circuitry of imaging system 20.

Initially, at step S301, x-ray tube 21 emits imaging radiation. In some embodiments, the imaging radiation is emitted toward a patient disposed in a first position. The patient may be positioned on table 30 such that a portion of the patient lies between x-ray tube 21 and imaging device 23.

Imaging device 23 then acquires an image based on the imaging radiation in step S302. More particularly, portions of the imaging radiation may be attenuated by objects located between x-ray tube 21 and imaging device 23. Consequently, the imaging radiation received by imaging device 23 includes gradients that depend on the composition of the objects. These gradients are reflected in the acquired image and thereby represent the objects.

Next, at step S303, treatment head 11 emits treatment radiation. The amount, direction, shape, and/or energy of the treatment radiation may comply with a previously-generated treatment plan. In some embodiments, the treatment radiation is emitted toward a patient disposed in the above-mentioned first position. According to some of these embodiments, the image acquired in step S302 is used prior to step S303 to verify that the position of the patient matches a position required by the treatment plan.

X-ray tube 21 and imaging device 23 are moved independently of treatment head 11 in step S304. X-ray tube 21 and imaging device 23 may be moved in step S304 to acquire another image usable to verify a position of a patient disposed on table 30. The movement in step S304 may comprise rotating support 22 of imaging system 20. Flow may return to step S301 after step S304.

According to some embodiments, treatment head 11 may be rotated around axis 14 at any time during process 300. In some embodiments of process steps 300, x-ray tube 21 is not coupled to gantry 12 but is used to emit radiation towards a patient that is disposed in a position towards which treatment head 11 will emit treatment radiation. Imaging device 23 may or may not be coupled to gantry 12 according to these embodiments.

Figure 4:
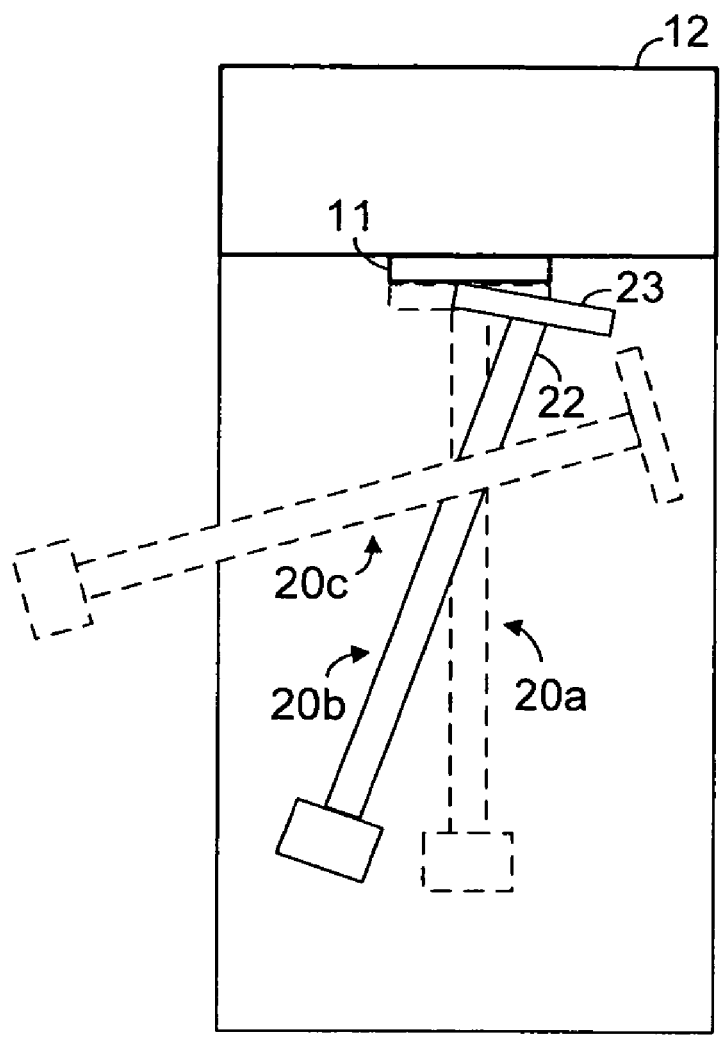
FIG. 4 is a view illustrating movement of an imaging system according to some embodiments.

FIG. 4 illustrates the movement of imaging system 20 according to some embodiments. Imaging system 20a is depicted under treatment head 11, which is drawn so as to include accessory tray 13 of FIG. 1. Imaging device 23 of imaging system 20a is located extremely close to, if not touching, treatment head 11.

According to some embodiments, imaging device 23 is moved with respect to support 22 as imaging system 20 rotates to the position indicated by imaging system 20b. The movement may be accomplished using a controllable tilt joint disposed between imaging device 23 and support 21. This movement may avoid a collision between treatment head 11 and imaging device 23. The movement may also allow imaging device 23 to be positioned closer to treatment head 11 when in the position shown by imaging system 20a than would otherwise be possible. Imaging device 23 may then return to its original position with respect to support 22 as shown by imaging system 20c.

Figure 5:
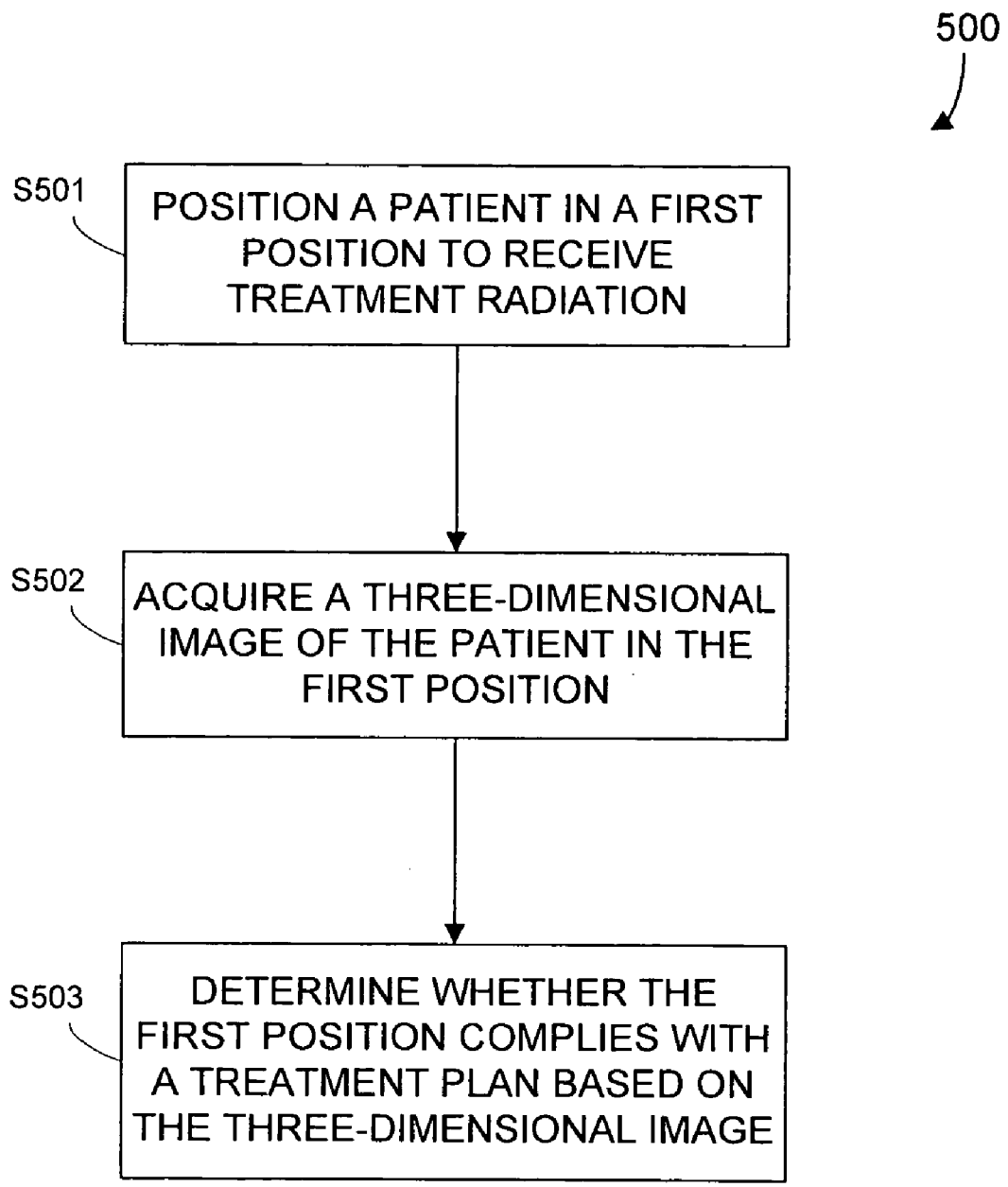
FIG. 5 is a flow diagram of process steps according to some embodiments.

FIG. 5 is a flow diagram of process steps 500 according to some embodiments. Process steps 500 may be embodied as described above with respect to process steps 300.

At step S501, a patient is positioned in a first position to receive treatment radiation. The first position may comply with a pre-established treatment plan. The patient may be positioned on table 30 using any currently- or hereafter-know patient positioning method.

A three-dimensional image of the patient is then acquired at step S502. The three-dimensional image may be acquired by rotating imaging system 20 around a region of interest to acquire a plurality of projection images of the patient in the first position from a variety of perspectives. For example, a first projection image may be acquired using imaging device 23 located at a first position relative to the patient, and a second projection image may be acquired using imaging device 23 located at a second position relative to the patient. Next, the three-dimensional image is created based on the plurality of projection images.

Based on the three-dimensional image, it is determined in step S503 whether the first position complies with a treatment plan. In one example, a processor located within system 1 determines a difference between the first position and a position required by the treatment plan by comparing an image of the planned treatment volume to the three-dimensional image. In another example, a location of a body of interest such as a tumor is confirmed using the acquired three-dimensional image. Any suitable system for determining whether the first position complies with a treatment plan may be employed in step S503. Treatment head 11 may then be used to deliver treatment radiation to the patient if it is determined that the first position complies with the treatment plan.

According to some embodiments, the patient is moved from the first position to a second position if it is determined at step S503 that the first position does not comply with the treatment plan. A second three-dimensional image of the patient in the second position may then be acquired and used to determine whether the second position complies with the treatment plan.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. An apparatus compfising:
   a treatment head to emit treatment radiation towards a patient;
   an x-ray tube to emit imaging radiation towards the patient;
   an imaging device to acquire an image based on the imaging radiation;
   a movable joint coupled to the imaging device; and
   a support coupled to the x-ray tube and to the movable joint, the support being rotatable to rotate the x-ray tube and the imaging device about an axis,
   wherein the movable joint is movable to move the imaging device with respect to the support to avoid a collision with the treatment head,
   wherein the x-ray tube and the imaging device are moveable independently of the treatment head, and
   wherein the imaging device is moveable between the treatment head and the patient.

2. An apparatus according to claim 1, further comprising:
   a gantry coupled to the treatment head, the gantry rotatable to rotate the treatment head about a first axis.

3. An apparatus according to claim 2, wherein the axis and the first axis are identical.

4. An apparatus according to claim 2, further comprising:
   a rotating coupling to couple the support to the gantry.

5. An apparatus according to claim 1, the imaging device to acquire the image based also on the treatment radiation.

6. An apparatus according to claim 1, the imaging device to acquire a plurality of images based on the imaging radiation, the plurality of images usable to create a tree-dimensional cone beam reconstruction image.

7. A method comprising:
   emitting imaging radiation towards a patient using an x-ray tube;
   acquiring an image based on the imaging radiation using an imaging device;
   emitting treatment radiation towards the patient using a treatment head; moving a support coupled to the x-ray tube and to the imaging device to move the x-ray tube and the imaging device independently of the treatment head;
   moving a movable joint coupled to the support and to the imaging device to move the imaging device with respect to the support to avoid a collision with the treatment head; and
   moving imaging device between the treatment head and the patient.

8. A method according to claim 7, further comprising:
   rotating the treatment head about a first axis by rotating a gantry coupled to the treatment head.

9. A method according to claim 8, further comprising:
   rotating the x-ray tube and the imaging device about a second axis by rotating the support.

10. A method according to claim 9, wherein the first axis and the second axis are identical.

11. A method according to claim 7, further comprising:
    rotating the x-ray tube and the imaging device about an axis by rotating the support.

12. A method according to claim 7, further comprising:
    acquiring the image based also on the treatment radiation using the imaging device.

13. A method according to claim 7, further comprising:
    acquiring a plurality of images based on the imaging radiation using the imaging device; and
    creating a three-dimensional cone beam reconstruction image based on the plurality of images.

* * * * *